United States Patent
Hunt et al.

(10) Patent No.: US 11,807,826 B2
(45) Date of Patent: *Nov. 7, 2023

(54) LUBRICATING BASE OILS FROM ESTERIFIED ALKOXYLATED POLYOLS USING SATURATED LONG-CHAIN FATTY ACIDS

(71) Applicant: Tetramer Technologies, LLC, Pendleton, SC (US)

(72) Inventors: Zachary Hunt, Simpsonville, SC (US); Peter Gennaro, Mount Pleasant, SC (US); Jeffrey R. DiMaio, Pendleton, SC (US); Benjamin Bergmann, Liberty, SC (US)

(73) Assignee: Universtiy of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/552,418

(22) Filed: Dec. 16, 2021

(65) Prior Publication Data

US 2022/0106535 A1  Apr. 7, 2022

Related U.S. Application Data

(63) Continuation of application No. 16/429,184, filed on Jun. 3, 2019, now Pat. No. 11,230,682.
(Continued)

(51) Int. Cl.
*C10M 105/44* (2006.01)
*C10M 101/04* (2006.01)
(Continued)

(52) U.S. Cl.
CPC ........ *C10M 105/44* (2013.01); *C10M 101/04* (2013.01); *C10M 2207/301* (2013.01);
(Continued)

(58) Field of Classification Search
CPC .............. C10M 105/44; C10M 101/04; C10M 2207/301; C10M 2209/043;
(Continued)

(56) References Cited

U.S. PATENT DOCUMENTS 3,337,595 A   8/1967  Lamont
3,530,070 A   9/1970  Rosevear et al.
(Continued)

FOREIGN PATENT DOCUMENTS

EP   0353928   2/1990
EP   0938536   9/1999
(Continued)

OTHER PUBLICATIONS

Anonymous, Polysorbate, Wikipedia, May 24, 2017, URL:https://en.wikipedia.org/wiki/Polysorbate.

*Primary Examiner* — James C Goloboy
*Assistant Examiner* — Francis C Campanell
(74) *Attorney, Agent, or Firm* — Burr & Forman LLP; Douglas L. Lineberry

(57) ABSTRACT

The present disclosure relates to methods and compositions for making bio-based, biodegradable, and non-bioaccumulating lubricating base oils generated by esterifying alkoxylated polyols (average alkoxylation ≥3) with long-chain (≥C14) saturated and unsaturated fatty acids (FA) or fatty acids modified using industry recognized techniques.

19 Claims, 13 Drawing Sheets

Related U.S. Application Data

(60) Provisional application No. 62/680,030, filed on Jun. 4, 2018.

(51) Int. Cl.
  *C10N 40/04* (2006.01)
  *C10N 40/12* (2006.01)

(52) U.S. Cl.
  CPC ... *C10M 2209/043* (2013.01); *C10N 2040/04* (2013.01); *C10N 2040/12* (2013.01)

(58) Field of Classification Search
  CPC .. C10M 2207/2825; C10M 2207/2835; C10M 2207/2895; C10M 2209/1033; C10M 2209/1045; C10M 2209/1055; C10M 107/34; C10M 105/38; C10N 2040/04; C10N 2040/12; C10N 2020/011; C10N 2020/017; C10N 2020/02; C10N 2020/04; C10N 2020/081; C10N 2040/16; C10N 2050/10; C07C 69/30; C07C 69/33
  USPC ........................................... 508/463
  See application file for complete search history.

(56) References Cited

U.S. PATENT DOCUMENTS

| | | | |
|---|---|---|---|
| 3,871,837 A | 3/1975 | Bedague et al. | |
| 4,031,118 A | 6/1977 | Miller | |
| 4,983,329 A | 1/1991 | Cooper | |
| 5,494,693 A | 2/1996 | Cooper | |
| 5,571,935 A | 11/1996 | Sekula et al. | |
| 5,618,779 A | 4/1997 | Klein et al. | |
| 5,645,881 A | 7/1997 | Tancibok et al. | |
| 5,681,939 A | 10/1997 | Ferenz | |
| 5,916,854 A * | 6/1999 | Inaya ................... | C10M 111/00 508/491 |
| 6,002,030 A | 12/1999 | Valbert | |
| 6,268,010 B1 | 7/2001 | Sekula | |
| 9,011,961 B2 | 4/2015 | Strecker et al. | |
| 11,230,682 B2 * | 1/2022 | Hunt ....................... | C07C 69/33 |
| 2003/0072864 A1 | 4/2003 | Sekula | |
| 2011/0247578 A1 | 10/2011 | Jansson et al. | |
| 2018/0010060 A1 | 1/2018 | Zannoni et al. | |

FOREIGN PATENT DOCUMENTS

| | | |
|---|---|---|
| WO | WO1995002659 | 1/1995 |
| WO | WO2012134792 | 10/2012 |
| WO | WO2012158503 | 11/2012 |
| WO | WO2014124698 | 8/2014 |

* cited by examiner

| | Table A. Examples 1-24 | | | | | | | |
|---|---|---|---|---|---|---|---|---|
| | Example | Pour Point (°C) | Kinematic Viscosity | | | Fatty Acid Content | | | |
| | | | KV 40 | KV 100 | VI | C-12 | C-14 | C-16 | C-18 |
| PG-10 | 1 | 7.18 | 67.65 | 12.5 | 186 | 0.0000 | 0.3181 | 0.3392 | 0.3426 |
| | 2 | -11.07 | 58.05 | 11 | 185 | 0.0000 | 0.9801 | 0.0044 | 0.0154 |
| | 3 | -37.52 | 53.65 | 9.9 | 173 | 0.9693 | 0.0115 | 0.0000 | 0.0192 |
| | 4 | -9.82 | 59.1 | 10.9 | 179 | 0.3035 | 0.3377 | 0.3488 | 0.0099 |
| | 5 | 15.22 | 69.5 | 12.5 | 181 | 0.0000 | 0.0000 | 0.4817 | 0.5183 |
| | 6 | -0.97 | 61.15 | 11.4 | 183 | 0.3169 | 0.3342 | 0.0087 | 0.3403 |
| | 7 | -38.32 | 55 | 10.25 | 178 | 0.9862 | 0.0138 | 0.0000 | 0.0000 |
| | 8 | 10.56 | 74 | 13.2 | 182 | 0.1212 | 0.1299 | 0.1279 | 0.6210 |
| | 9 | -25.12 | 58.4 | 10.8 | 179 | 0.4904 | 0.5016 | 0.0040 | 0.0039 |
| | 10 | 20.62 | 76.85 | 13.4 | 179 | 0.0000 | 0.0000 | 0.0077 | 0.9923 |
| | 11 | -7.9 | 64.9 | 11.7 | 178 | 0.1230 | 0.6201 | 0.1267 | 0.1302 |
| | 12 | 3.07 | 68.5 | 12.3 | 180 | 0.1138 | 0.1258 | 0.6183 | 0.1422 |
| | 13 | -23.67 | 56 | 10.5 | 180 | 0.4840 | 0.4982 | 0.0043 | 0.0136 |
| | 14 | -12.72 | 59.7 | 11 | 179 | 0.6098 | 0.1324 | 0.1289 | 0.1290 |
| | 15 | -13.04 | 60.3 | 11.1 | 179 | 0.0112 | 0.9836 | 0.0052 | 0.0000 |
| | 16 | -0.72 | 63.4 | 11.6 | 180 | 0.0042 | 0.4839 | 0.4941 | 0.0178 |
| | 17 | 8.37 | 68 | 12.3 | 181 | 0.0058 | 0.4872 | 0.0108 | 0.4962 |
| | 18 | 1.1 | 64.6 | 11.8 | 181 | 0.2462 | 0.2637 | 0.2503 | 0.2398 |
| | 19 | -5.81 | 58.6 | 9.9 | 155 | 0.4670 | 0.0000 | 0.5131 | 0.0199 |
| | 20 | 8.97 | 63.2 | 11.6 | 181 | 0.0000 | 0.0000 | 0.9750 | 0.0250 |
| | 21 | 21.96 | 72.7 | 13.2 | 186 | 0.0000 | 0.0000 | 0.0000 | 1.0000 |
| | 22 | 8.31 | 65.35 | 12 | 183 | 0.0000 | 0.0000 | 0.9679 | 0.0321 |
| | 23 | 6.35 | 61.85 | 11.5 | 183 | 0.4795 | 0.0000 | 0.0110 | 0.5095 |
| | 24 | 7.69 | 62.8 | 11.5 | 180 | 0.3095 | 0.0000 | 0.3419 | 0.3487 |

FIGURE 3

| | Table B. Examples 25-48 |||||||
|---|---|---|---|---|---|---|---|---|
| | Example | Pour Point (°C) | Kinematic Viscosity ||| Fatty Acid Content ||||
| | | | KV 40 | KV 100 | VI | C-12 | C-14 | C-16 | C-18 |
| PG-05 | 25 | 16.77 | 57.25 | 10.5 | 175 | 0.0000 | 0.3155 | 0.3330 | 0.3514 |
| | 26 | 1.08 | 48.9 | 9.2 | 173 | 0.0000 | 0.9858 | 0.0142 | 0.0000 |
| | 27 | -19.74 | 40.8 | 7.9 | 169 | 0.9718 | 0.0282 | 0.0000 | 0.0000 |
| | 28 | 0.07 | 47.2 | 8.9 | 172 | 0.3443 | 0.3319 | 0.3238 | 0.0000 |
| | 29 | 24.11 | 61.7 | 11.2 | 177 | 0.0000 | 0.0000 | 0.4839 | 0.5161 |
| | 30 | 8.76 | 50.4 | 9.5 | 176 | 0.3129 | 0.3322 | 0.0174 | 0.3376 |
| | 31 | -21.3 | 40.15 | 7.9 | 173 | 0.9646 | 0.0198 | 0.0000 | 0.0156 |
| | 32 | 22.7 | 57.95 | 10.5 | 173 | 0.1198 | 0.1210 | 0.1251 | 0.6341 |
| | 33 | -10.02 | 43.1 | 8.45 | 177 | 0.4985 | 0.5015 | 0.0000 | 0.0000 |
| | 34 | 30.69 | | | | 0.0000 | 0.0000 | 0.0080 | 0.9920 |
| | 35 | 5.01 | 48 | 9.2 | 178 | 0.1241 | 0.6059 | 0.1320 | 0.1380 |
| | 36 | 13.73 | 53.5 | 10.1 | 180 | 0.1187 | 0.1355 | 0.5988 | 0.1470 |
| | 37 | -10.62 | 43 | 8.3 | 172 | 0.4802 | 0.5117 | 0.0080 | 0.0000 |
| | 38 | -4.43 | 45.6 | 8.8 | 176 | 0.6091 | 0.1306 | 0.1275 | 0.1329 |
| | 39 | -1.48 | 48.1 | 9.1 | 174 | 0.0065 | 0.9830 | 0.0063 | 0.0042 |
| | 40 | 9.58 | 52.7 | 9.9 | 177 | 0.0000 | 0.4974 | 0.4876 | 0.0150 |
| | 41 | 16.9 | 57.1 | 10.7 | 181 | 0.0037 | 0.4828 | 0.0083 | 0.5052 |
| | 42 | 10.15 | 51 | 9.7 | 179 | 0.2367 | 0.2498 | 0.2507 | 0.2628 |
| | 43 | 3.3 | 48.9 | 9.2 | 173 | 0.4580 | 0.0179 | 0.4971 | 0.0270 |
| | 44 | 17.34 | 59.55 | 10.8 | 175 | 0.0000 | 0.0000 | 0.9717 | 0.0283 |
| | 45 | 30.65 | | | | 0.0000 | 0.0000 | 0.0290 | 0.9710 |
| | 46 | 17.23 | 57 | 10.6 | 179 | 0.0000 | 0.0000 | 0.9710 | 0.0290 |
| | 47 | 13.92 | 51 | 9.7 | 179 | 0.4660 | 0.0000 | 0.0341 | 0.4999 |
| | 48 | 14.55 | 53.15 | 9.9 | 175 | 0.3102 | 0.0000 | 0.3317 | 0.3581 |

FIGURE 4

Table C. Examples 49-72

| | Example | Pour Point (°C) | Kinematic Viscosity | | | Fatty Acid Content | | | |
|---|---|---|---|---|---|---|---|---|---|
| | | | KV 40 | KV 100 | VI | C-12 | C-14 | C-16 | C-18 |
| PG-03 | 49 | 22.76 | 58.9 | 9.7 | 149 | 0.0000 | 0.3176 | 0.3300 | 0.3524 |
| | 50 | 9.06 | 49.1 | 8.2 | 140 | 0.0000 | 0.9813 | 0.0100 | 0.0087 |
| | 51 | -9.73 | 40.2 | 7 | 135 | 0.9215 | 0.0354 | 0.0141 | 0.0290 |
| | 52 | 7.32 | 49.1 | 8 | 133 | 0.3312 | 0.3325 | 0.3260 | 0.0104 |
| | 53 | 30.38 | | | | 0.0090 | 0.0088 | 0.4778 | 0.5044 |
| | 54 | 14.82 | 51.7 | 8.6 | 143 | 0.3318 | 0.3151 | 0.0197 | 0.3334 |
| | 55 | -11.43 | 39.9 | 7 | 137 | 0.9509 | 0.0254 | 0.0000 | 0.0237 |
| | 56 | 26.97 | 58.8 | 9.6 | 147 | 0.1701 | 0.1208 | 0.1209 | 0.5882 |
| | 57 | -2.16 | 43.4 | 7.5 | 140 | 0.5155 | 0.4845 | 0.0000 | 0.0000 |
| | 58 | 36.13 | | | | 0.0000 | 0.0000 | 0.0092 | 0.9908 |
| | 59 | 14.05 | 51.6 | 8.6 | 144 | 0.1145 | 0.5996 | 0.1262 | 0.1597 |
| | 60 | 20.55 | 56.8 | 9.5 | 151 | 0.1188 | 0.1362 | 0.6014 | 0.1436 |
| | 61 | -2.32 | 43.5 | 7.6 | 143 | 0.4962 | 0.5038 | 0.0000 | 0.0000 |
| | 62 | 3.39 | 45.7 | 7.8 | 140 | 0.5903 | 0.1382 | 0.1280 | 0.1435 |
| | 63 | 8.54 | 48.8 | 7.8 | 128 | 0.0241 | 0.9759 | 0.0000 | 0.0000 |
| | 64 | 16.76 | 53.5 | 9 | 149 | 0.0000 | 0.5021 | 0.4823 | 0.0156 |
| | 65 | 23.48 | 59.5 | 9.7 | 147 | 0.0080 | 0.4729 | 0.0130 | 0.5061 |
| | 66 | 16.74 | 53.9 | 8.9 | 144 | 0.2353 | 0.2625 | 0.2585 | 0.2436 |
| | 67 | 17.66 | 52.6 | 8.8 | 146 | 0.4946 | 0.0000 | 0.0000 | 0.5054 |
| | 68 | 24.68 | 61.3 | 9.8 | 144 | 0.0137 | 0.0000 | 0.9488 | 0.0375 |
| | 69 | 36.67 | | | | 0.0000 | 0.0000 | 0.0299 | 0.9701 |
| | 70 | 25.54 | 61.8 | 9.9 | 145 | 0.0000 | 0.0000 | 0.9520 | 0.0480 |
| | 71 | 18.76 | 52 | 8.8 | 148 | 0.4798 | 0.0000 | 0.0000 | 0.5202 |
| | 72 | 20.7 | 55.5 | 9.2 | 147 | 0.3210 | 0.0000 | 0.3304 | 0.3486 |

FIGURE 5

| Table D. Examples 73-79 |||||||||
|---|---|---|---|---|---|---|---|---|
| Example | 73 | 74 | 75 | 76 | 77 | 78 | 79 | JD HyGard |
| PO # | 10 | 10 | 10 | 10 | 10 | 5 | 5 | N/A |
| Fatty Acid | HO Soybean | Soybean | Canola | Coconut | Lauric | Lauric | Oleic | N/A |
| Pour Point (°C) | -24 | -15 | -42 | -15 | -36 | -24 | -42 | -39 |
| Copper Strip Corrosion | 1B | 1B | 1B | 1B | 1B | 1B | 1A | 1A |
| KV 40 °C (cSt) | 68.35 | 59.36 | 65.34 | 58.02 | 55.76 | 38.66 | 54.22 | 58.71 |
| KV 100 °C (cSt) | 13.11 | 11.93 | 12.78 | 10.59 | 10.2 | 7.559 | 10.81 | 9.283 |
| Viscosity Index | 197 | 202 | 200 | 175 | 173 | 167 | 195 | 139 |
| 4 Ball Wear Scar (mm) | 0.204 | 0.56 | 0.21 | 0.494 | 0.482 | 0.519 | 0.652 | 0.192 |

FIGURE 9

| Table E. Examples 80-84 | | | | | |
|---|---|---|---|---|---|
| Example | Functional FA (%) | Pour Pt. (°C) | KV40 (cSt) | KV100 (cSt) | VI |
| 80 | 0 | -17.72 | 58.35 | 10.8 | 179 |
| 81 | 5 | -18.23 | 72.8 | 11.8 | 158 |
| 82 | 10 | -18.59 | 85.9 | 13.1 | 153 |
| 83 | 5 | -18.50 | 70.2 | 11.0 | 148 |
| 84 | 10 | -17.77 | 77.5 | 12.0 | 150 |

FIGURE 10

| Table F. Example 85 | | | |
|---|---|---|---|
| Test | Envirotemp FR-3 | Envirotemp 200 | Example 85 |
| Dielectric BD Disk | 47 | 43 | 50 |
| Color | 0.5 | <1.0 | 0.5 |
| Interfacial Tension (25°C) | 27 | 29 | 24.9 |
| Flash Point (°C) | 330 | 270 | 303 |
| Fire Point (°C) | 360 | 306 | 324 |
| Pour Point (°C) | -21 | -50 | -42 |
| Specific gravity (15°C) | 0.92 | 0.97 | 0.94 |
| KV100 (cSt) | 8 | 5.6 | 10.8 |
| KV40 (cSt) | 33 | 29 | 54.2 |
| Visual examination | clear light green | bright and clear | clear |
| Acid Value (mg KOH/g) | 0.042 | 0.03 | 0.18 |
| Water Content (ppm) | 20 | 60 | 680 |

FIGURE 12

| Table G. Examples 86-88 | | | | |
|---|---|---|---|---|
| Example | Pour Pt. (°C) | KV40 (cSt) | KV100 (cSt) | VI |
| 86 | -1.1 | 55.2 | 11.2 | 201 |
| 87 | 36.51 | N/A | N/A | N/A |
| 88 | -15.81 | 52.65 | 10.6 | 196.5 |

FIGURE 13

LUBRICATING BASE OILS FROM ESTERIFIED ALKOXYLATED POLYOLS USING SATURATED LONG-CHAIN FATTY ACIDS

This disclosure was developed with the use of funds from the National Science Foundation Grant 1555998, Department of Energy Grant DE-SC0018751 and USDA Grant 2018-33610-28260. The Government has certain rights in the invention.

FIELD OF THE INVENTION

The present disclosure relates to methods and compositions for making bio-based, biodegradable, and non-bioaccumulating lubricating base oils generated by esterifying alkoxylated polyols (average alkoxylation ≥3) with long-chain (≥C14) saturated and unsaturated fatty acids (FA) or fatty acids modified using industry recognized techniques.

BACKGROUND OF THE INVENTION

Lubricant demand and usage are expected to steadily increase over the coming years. Along with the increased demand, performance requirements are also changing, leading to the development of novel and high-performance lubricants. Lubricants are expected to carry greater loads at longer drain intervals while simultaneously providing increased mechanical efficiency and lower risk of environmental contamination. Because of the increased expectations, original equipment manufacturers (OEM) and end users are in need of lubricants that are significantly more robust than the Group I and Group II petroleum lubricants that are widely available at low cost.

Current replacement options are severely hydrotreated mineral oils (Group III/III+), polyalphaolefin (PAO, Group IV), and other synthetic lubricants (Group V). The Group V oils encompass a wide range of materials including vegetable oils, synthetic esters, polyalkylene glycols, and naphthenic oils. All of the replacement options have associated cost increases and/or material specific performance limitations relative to the more common Group I/II base oils.

Viscosity is the one of the most important physical property for a lubricating oil. Different applications require varied viscosities based on the operating conditions of a given system.

For petroleum derived lubricants (Group III/III+ and PAO) high viscosity lubricants (>ISO VG 150) are costly to produce and have relatively poor viscosity indices, while ultra-low viscosity lubricants (<ISO VG 22) have significant amounts of volatile components creating issues with fire and flash stability and evaporative loss. The best applications for these lubricants are those that require ISO VG 32-100, are not run at excessive temperatures, and are not areas of environmental concern.

Synthetic esters can be made to span a broad range of viscosities but are generally costlier on a per kg basis. Additionally, to meet higher viscosities (ISO VG>100) pour point is severely affected, limiting operational conditions for the lubricants. Synthetic esters tend to have high flash and fire points and are generally more environmentally friendly than petroleum derived lubricants. The best applications for these lubricants are those that require ISO VG 22-46, are not prone to prolonged high load use, and require high temperature safety due to fire risk.

Vegetable oils are environmentally friendly, fire and flash stable, and provide excellent wear resistance and lubricity. The most significant drawback to them is thermal and oxidative stability. Vegetable oils tend to oxidize rapidly at elevated temperatures and tend to crystallize or solidify at near zero temperatures. The best applications of these lubricants are those that require ISO VG 32-68, where temperatures are strictly controlled, and where contamination or leaks are of health and environmental concern.

Various lubricants have been disclosed. For example, U.S. Pat. No. 3,337,595 discloses the making of fatty acid esters of propoxylated glycerol for use as defoaming aids. The preferred embodiment of the art is diesters of propoxylated glycerol and blends of said diesters with fatty acid methyl esters and esters of polyethylene glycol.

U.S. Pat. No. 3,530,070 discloses the use of propoxylated polyols as synthetic lubricants. The compositional space encompasses multiple polyols (trimethylol propane, neopentyl glycol, pentaerythritol, dipentaerythritol, sorbitol, and glycerol) propoxylated up to an average of 72 PO units per mole of polyol and esterified to various fatty acids (≤C12).

U.S. Pat. No. 4,031,118 is concerned with ester containing processes and compositions. The compositions disclosed are high MW (1000-10000 g/mol) polyether polyols esterified with very long chain (≥C30) fatty acids.

U.S. Pat. No. 5,916,854 discloses the use and composition of interesterified and alkoxylated lubricating oils. The compositions are product by process entailing the interesterification of natural oils with glycerol or free fatty acids with simultaneous alkoxylation. The resultant products are a blend of many different compositions including monoesters, diesters, and linear esters.

PCT WO1995002659 discloses lubricating oil compositions for use as hydraulic fluids. Two processes are used to generate the claimed compositions:
  a.) Propoxylation of glycerol to an average of <3 PO units per glycerol with preferred embodiments of 1 PO unit per glycerol followed by esterification with FA from C6-C24
  b.) One pot process like that listed under U.S. Pat. No. 5,916,854 creating product by process.

PCT WO2012134792 discloses a lubricant composition comprising polymers of glycerol that have been propoxylated to an average of 6-15 PO units followed by esterification with FA from C8-C15. Preferred claims are alkoxylates (PO 8-12) and FA esters (C9-11) of diglycerol and triglycerol.

PCT WO2014124698 concerns the composition and use of ester lubricants. The compositions claimed and described concern propoxylated pentaerythritol esterified with various fatty acids.

What is needed in the art is the use of long-chain fatty acid in significant quantities in combination with alkoxylated polyols while maintaining pour point temperatures and viscosities characteristic of a lubricating oil. Prior disclosures have utilized room temperature fluid or very low melting FA to control thermal and viscometric properties of the base oil. This disclosure substantially utilizes high melting FA, controlling thermal and viscometric properties by manipulating the degree of alkoxylation and minor fatty acid components of the esterification product.

SUMMARY OF THE INVENTION

The above objectives are accomplished according to the present disclosure by providing in a first embodiment, a synthetic ester lubricating base oil. The base oil may comprise at least one alkoxylated polyol, wherein the average degree of alkoxylation is from ≥3 and at least one fatty acid, wherein the fatty acid is substantially long-chain, equal to or greater than C14. Further the at least one alkoxylated polyol may comprise glycerol, trimethylol propane, neopentyl glycol, or sorbitol. Further yet, the at least one alkoxylated polyol may comprise propoxylated glycerol. Still yet, the at least one fatty acid may be substantially fully saturated. Further still, the at least one fatty acid may be substantially unsaturated. Yet still, the at least one fatty acid may comprise fatty acids with chain lengths <C14. Further again, the source for the at least one fatty acid may be substantially whole cut. Still again, the at least one fatty acid may be a dicarboxylic acid. Yet again, the at least one substantially fully saturated fatty acid may comprise 12-hydroxystearic acid. Again still, the at least one fatty acid may be functionalized and the functionalization may comprise epoxidation, maleination, metathesis, amidation, halogenation, hydration, estolide formation, or vulcanization. Again still, the lubricating base oil may have a pour point of at or below −10° C. Still yet further, the lubricating base oil may be at least 60 percent biodegradable. Yet again further, the lubricating base oil may be at least 50 percent bio-based. Further yet still, the lubricating base oil may form a base for a grease. Yet again still, the lubricating base oil may comprises a process oil or rubber extender oil. Yet still, the lubricating base oil may comprise a dielectric fluid.

In a further embodiment, a method is provided for forming a synthetic ester lubricating base oil. The method includes alkoxylating at least one polyol backbone, wherein the average degree of alkoxylation is from ≥3 and esterifying the at least one alkoxylated polyol backbone with at least one fatty acid, wherein the at least one fatty acid is substantially long-chain, equal to or greater than C12. Further, the at least one fatty acid may be saturated. Yet further, the at least one fatty acid may be unsaturated. Still yet, the at least one fatty acid may be substantially long-chain, equal to or greater than C14. Yet again, the method may include functionalizing the at least one fatty acid. Still yet further, functionalization may include epoxidation, maleination, metathesis, amidation, halogenation, hydration, estolide formation, hydroxy functionalization, or vulcanization. Again further, the method includes forming the lubricating base oil into a base for a grease.

BRIEF DESCRIPTION OF THE DRAWINGS

The construction designed to carry out the invention will hereinafter be described, together with other features thereof. The disclosure will be more readily understood from a reading of the following specification and by reference to the accompanying drawings forming a part thereof, wherein an example of the disclosure is shown and wherein:

FIG. 3 shows Table A: Base oil property data for examples 1-24.

FIG. 4 shows Table B: Base oil property data for examples 25-48.

FIG. 5 shows Table C: Base oil property data for examples 49-72.

FIG. 9 shows Table D: Lubricant specific data comparison for examples 73-79 and John Deere HyGard Transmission and Hydraulic OIL.

FIG. 10 shows Table E: Base oil properties for modified base oil examples 80-84.

FIG. 12 shows Table F: Dielectric fluid test data comparison for example 85 and two commercial biodegradable dielectric fluids.

FIG. 13 shows Table G: Base oil data for esterified ethoxylated glycerol samples with coconut, stearic, lauric acids.

Figure 1:
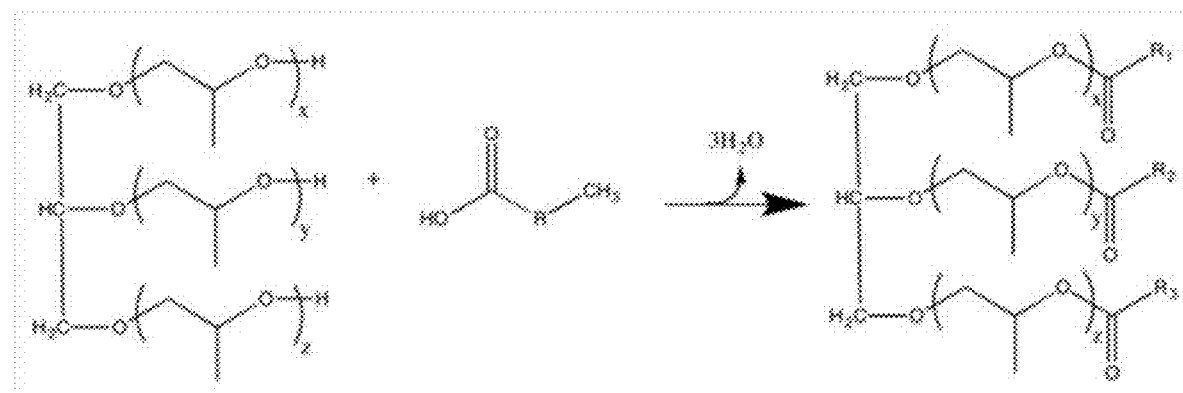
FIG. 1 shows Scheme A: Reaction scheme for the synthesis of esterified propoxylated glycerol from the propoxylated glycerol and fatty acids base components.

It will be understood by those skilled in the art that one or more aspects of this disclosure can meet certain objectives, while one or more other aspects can meet certain other objectives. Each objective may not apply equally, in all its respects, to every aspect of this disclosure. As such, the preceding objects can be viewed in the alternative with respect to any one aspect of this disclosure. These and other objects and feature of the disclosure will become more fully apparent when the following detailed description is read in conjunction with the accompanying figures and examples. However, it is to be understood that both the foregoing summary of the disclosure and the following detailed description are of a preferred embodiment and are not restrictive of the disclosure or other alternate embodiments of the disclosure. In particular, while the disclosure is described herein with reference to a number of specific embodiments, it will be appreciated that the description is illustrative of the disclosure and is not constructed as limiting of the disclosure. Various modifications and applications may occur to those who are skilled in the art, without departing from the spirit and the scope of the disclosure, as described by the appended claims. Likewise, other objects, features, benefits and advantages of the present disclosure will be apparent from this summary and certain embodiment described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the disclosure will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The lubricating base oils of the present disclosure combine the lubricity and wear resistance of vegetable oils, the low temperature pour points of synthetic esters, and the range of viscosities of the "synthetic" petroleum derivatives, while being lower cost than both current synthetic esters and Group III+/PAO lubricants.

By utilizing long chain fatty acid(s) in conjunction with alkoxylated polyol(s), this disclosure generates base oils that have high bio-based content (>60 wt. %, such as >65, >70, >75, >80, >85, >90, >95, etc.), and high biodegradability. Bio-based content refers to materials which are derived from biological products or renewable domestic agricultural materials (including plant, animal, and marine materials) or forestry materials or an intermediate feedstock. Biodegradability refers to the ability of a material to be decomposed by bacteria or other living organisms.

The above objectives are accomplished according to the present disclosure by providing in a first embodiment, a lubricating base oil. The lubricating base oil may include an alkoxylated polyol combined with at least one saturated fatty acid source to form an esterified alkoxylated polyol. Further, the esterified alkoxylated polyol comprises esterified propoxylated glycerol (EPG). Still further, the lubricating base oil is at least 40 percent biodegradable, such as for purposes of example only and not intended to be limiting 45 percent, 50, 55, 60, 65, 70, 75, 80, 85, 90, 95, etc., more preferably the lubricating base oil is at least 50 percent biodegradable, and most preferably the lubricating base oil is at least 60 percent biodegradable. Yet further, the base oil has an average degree of alkoxylation of greater than or equal to 3, such as 4, 5, 6, 7, 8, 9, 10 or greater. Further still, at least one fatty acid source comprising the oil is substantially long-chain (>C14, such as C15, C16, C17, C18, C19, C20, C21, C22, C23, C24, C25, C26, C27, C28, C29, C30, or longer) fatty acids. Even further, at least one fatty acid source comprising the oil is substantially unsaturated fatty acid. Even still further, the oil has a pour point at or below 0° C., and more preferably below −10° C., such as −15, −20, −25, −30, −35, −40, etc. Further yet, at least one fatty acid source may substantially be whole cut. Whole cut fatty acids are products of the direct fat splitting of natural oils and substantially comprise the native fatty acid composition of a representative natural oil. For the purposes of this disclosure, the whole cut fatty acid may be "cleaned" as understood by those of skill in the art and/or partially fractionated. Further, specific cuts, such as for purpose of example only but not intended to be limiting, high melt point cuts, may also be employed. Suitable whole cut fatty acids may be derived from vegetable or seed oils such as coconut oil, palm oil, palm kernel oil, palm fatty acid distillate soybean oil, rapeseed oil, canola oil, high oleic soybean oil, sunflower oil, corn oil, cottonseed oil, castor oil, olive oil, safflower oil, or linseed oil. Whole cut fatty acids may also be derived from animal oils such as fish oil, lard, tallow, or whale oil. Even further, the oil may include multifunctional fatty acids which may consist of dicarboxylic acids, hydroxy functional acids, or acids modified by techniques that may include but are not limited to epoxidation, maleination, metathesis, amidation, halogenation, hydration, or estolide formation.

In a further embodiment, a method is provided for forming a lubricating base oil. The method includes alkoxylating a polyol backbone and esterifying the alkoxylated polyol backbone with a saturated fatty acid, unsaturated fatty acid, or both to produce an esterified alkoxylated polyol. Further, the alkoxylated polyol comprises esterified propoxylated glycerol. Still further, the lubricating base oil is at least 60 percent biodegradable and may be 65, 70, 75, 80, 85, 90, or 95 percent or higher. Further yet, the base oil has an average degree of alkoxylation of equal to or greater than 3, such as 5, 7, etc. Still yet further, that at least one saturated fatty acid is equal to or greater than C12 saturated fatty acids, such as C13, C14, C15, C16, C17, C18, or higher. Even further, the saturated fatty acid is equal to or greater than C14, such as C15, C16, C17, C18, C19, C20, C22, C23, C24, C25, or higher. Yet still, the oil has a pour point of at or below −10° C., such as −15, −20, −25, −30, −35, −40, etc. Further yet, changing the feed ratio of at least one saturated fatty acid allows for tailoring properties of the lubricating base oil. Still further, that at least one saturated fatty acid source is whole cut. Still even further, at least one dicarboxylic acid is added as the esterified propoxylated polyol is formed. Yet still, that at least one saturated fatty acid comprises 12-hydroxystearic acid.

Some embodiments described herein are related to the synthesis and use of fatty acid esters of polyol alkoxylates, which possess viscosities characteristic of lubricating oils, have viscosity indices greater than 140, such as 145, 150, 155, 160, 165, 170, 175, 180, 185, 190, 195, 200, or higher, have pour points ≤0° C., such as −5, −10, −15, −20, −25, −30, −35, −40, etc. and are bio-based, biodegradable, and non-bioaccumulating alternatives to petroleum derived lubricating oils. A more preferred embodiment would consist of fatty acid esters of polyol alkoxylates with viscosity indices greater than 160, pour points ≤−10° C., bio-based content greater than 50%, and biodegradability greater than 40%, such as 45, 50, 55, 60, 65, 70, 75, 80, 85, 90, 95, or higher. Even further a more preferred embodiment would consist of fatty acid esters of polyol alkoxylates with viscosity indices greater than 180, pour points ≤−10° C., bio-based content greater than 55%, and biodegradability greater than 60%.

The polyol component of the present disclosure may be one or multiple common polyol substances such as, neopentyl glycol, trimethylol propane, glycerol, pentaerythritol, sorbitol, dipentaerythritol, or polyglycerols. The preferred polyol of this embodiment is glycerol.

The alkylene oxide component used to generate the polyol alkoxylate (polyether polyol) may consist of one or multiple alkylene oxides such as: ethylene oxide, propylene oxide, or butylene oxide. The alkoxylated polyol may contain ≥3 substituent alkoxy groups per polyol molecule. The preferred alkylene oxide of this embodiment is propylene oxide. The preferred degree of alkoxylation is ≥3 alkoxy groups per glycerol molecule, more preferably ≥5 alkoxy groups per glycerol molecule, and most preferably ≥10 alkoxy groups per glycerol molecule.

The fatty acid component of the esterified alkoxylated polyol may consist of saturated, unsaturated, or a combination of both saturated and unsaturated monobasic fatty acids with chain lengths of 4-24 carbons. The fatty acid component may also consist of saturated, unsaturated, or a combination therein of dibasic fatty acids with chain lengths ≥6 carbons. The fatty acid component may also consist of saturated, unsaturated, or a combination therein of hydroxy fatty acids. The fatty acid component may also consist of saturated, unsaturated, or a combination therein of branched fatty acids. The preferred fatty acids of this embodiment are both saturated and unsaturated monobasic fatty acids with chain lengths of 8-18 carbons.

The alkoxylated polyol may be synthesized utilizing common techniques known to those skilled in the art or may be acquired given a suitable commercially available source. The fatty acids may be derived from natural oils utilizing common techniques known to those skilled in the art or may be acquired from a suitable commercially available source. The esterification of the fatty acids and the alkoxylated polyol may be conducted with or without a catalyst utilizing techniques known to those skilled in the art. Non-catalyzed esterification may require the addition of molar excesses of fatty acid to the reaction mixture, reaction temperatures exceeding 150° C., application of vacuum to remove water, or a combination of said reaction parameters. Catalyzed esterification may be conducted at stoichiometric ratios of fatty acid to alcoholic hydroxyl, at temperatures below or above 150° C., at ambient pressure, or a combination of said reaction parameters. Suitable catalysts for the esterification of the alkoxylated polyol may include but are not limited to Iron (II) chloride, Titanium (IV) oxyacetylacetonate, Silica chloride, Graphene oxide, Sulfuric acid, Methanesulfonic acid, p-Tolunesulfonic acid, or Scandium (III) Triflate.

For the purposes of this embodiment the alkoxylated polyol was acquired from commercial sources and consisted of propoxylated glycerol with an average of 10 alkoxy groups per glycerol. The product is commonly supplied as 700 molecular weight glycerol-initiated polyether polyol (BASF: Pluracol GP730, Dow: Voranol 2070, Monument: Poly-G 30-240, Carpenter, Carpol GP700). For the purposes of this embodiment pure fatty acids utilized were selected from lauric (C12), myristic (C14), palmitic (C16), stearic (C18 sat.), and oleic (C18 unsat.). For the purposes of this embodiment whole cut fatty acids were also utilized and consist of coconut fatty acids, hydrogenated coconut fatty acids, soy fatty acids, canola fatty acids, and high oleic soy fatty acids.

The esterified propoxylated glycerol lubricant base oils of the present disclosure were prepared by charging an appropriate reaction vessel with the propoxylated glycerol and a 10% molar excess of the required fatty acid(s). The esterification was carried out at 240-250° C. and run under vacuum until the acid value of the reaction mixture was below about 15 mg KOH/g and the hydroxyl value of the reaction mixture was below about 20 mg KOH/g. Excess fatty acid and volatile reaction by products were then removed via short path distillation under vacuum and elevated temperature. Common ester purification techniques may be utilized in the absence of short path distillation. The ester product of the reaction was purified to an acid value <1 mg KOH/g with a preferred acid value <0.5 mg KOH/g, and a hydroxyl value <10 mg KOH/g with a preferred hydroxyl value <5 mg KOH/g.

The structure of the esterified propoxylated glycerol lubricating oil can be seen in Scheme A, see FIG. 1, which shows esterification of propoxylated glycerol (x+y+z=average degree of propoxylation) with fatty acid. One aspect of the present disclosure is that the polyether segments separating the glycerol (polyol) backbone and fatty acid chains characteristic of natural oils (synthetic esters) provide increased flexibility in the molecule enabling significant reductions in pour point compared to a natural oil or synthetic esters with an identical fatty acid profile. This lability in the molecule facilitates the use of higher fatty acids while maintaining the low pour points observed for esterified propoxylated glycerol lubricating oils. Another aspect of the present disclosure is that introduction of the polyether segments provides increased thermal and oxidative stability for the esterified propoxylated glycerol lubricants when compared to natural oils and non-neopentyl synthetic esters. A further aspect of the present disclosure is the use of long chain fatty acids to increase load carrying capacity of the lubricating base oil when compared to mid-chain fatty acid (C8-C11) synthetic esters. An additional aspect of the disclosure is an increase in detergency owing to the polyether segments of the base oil molecule as compared to common synthetic esters.

One aspect of the present disclosure is the functionalization of the fatty acid functionality of the esterified propoxylated glycerol lubricating base oil. Common techniques, known to those skilled in the art, may be used to modify the fatty acid chains to impart desired performance characteristics which may include epoxidation, maleination, metathesis, amidation, halogenation, hydration, estolide formation, or vulcanization.

One aspect of the present disclosure is the use of the esterified propoxylated glycerol as a lubricating base oil, either neat or as a formulated product, in Industrial Lubricants: gear oils, R&O compressor oils, R&O turbine oils; Automotive Oils: crankcase oils, transmission oils, gear oils; Metalworking Fluids; Marine Lubricants; Grease; Process Oils, or Dielectric Fluids.

A further aspect of the present disclosure is the use of esterified propoxylated glycerol base oils as biodegradable dielectric fluid. Dielectric fluids are used to cool, insulate and protect the internals of electronic devices. Typically, these fluids are used in transformers, capacitors, switches, etc. When used in a transformer, for example, dielectric fluids transport heat from the windings and core of the transformer or connected circuits to cooling surfaces.

Lubricants generally consist of liquid base oil and additives, whereas grease is a solid to semi-solid product consisting of lubricating oil (base oil) and thickener, unlike other lubricants. According to the ASTM (American Society for Testing and Materials), lubricating grease is a solid or semi-fluid substance containing a thickener agent and a lubricating liquid. In grease, the consistency of the product can be varied by thickening agents such as soap (calcium, lithium, and sodium), complex soap (calcium, lithium, lithium-calcium, aluminum), and bentone- or polyurea-based soap. The manufacturing of grease is a complex process involving various chemical reactions produced by different components. Grease are used as an alternative to liquid lubricants where space is restricted as well as to avoid the leaking and dripping associated with the liquid lubricants. Renewable and bio-based greases are desired but natural oils do not sufficiently structure the thickener leading to phase separation and early oiling out of grease compositions. Esterified propoxylated glycerol base oils utilizing diacids and hydroxy functional acids should have the viscosity and functional affinity for the thickener in a grease formulation limiting or eliminating the phase separation seen with other natural base oils.

Process oils or rubber extender oils are special mineral oils derived from refining base oils, mainly as a mixture of naphthenic, aromatic and paraffinic compounds. Process oils have low volatility, low oxidation, high saturation and color stability. They increase the stability and purity of finished products, making them suitable for application in industries such as tire, rubber, personal care products, polymers and textiles. They also have application as a raw material or as a processing aid for materials. In the tire and rubber industries, process oil and rubber extender oils functions as an internal lubricant to improve the blending of rubber formulations and can be used to make products softer, more flexible and even provide insulating properties. The demand for weather-resistant, flexible rubber products makes process oils and rubber extender oils an important ingredient in the production of automotive tires and other rubber products. Process oils make products softer, more flexible and even provide insulating properties. The demand for weather-resistant, flexible rubber products makes process oils an important ingredient in the production of automotive tires. Process oils also find use in the personal care industry. They lubricate, soften, smooth, extend, moisturize and add emollience to the finished product. Natural oils suitable for low temperature applications tend to consist of significant amounts polyunsaturated fatty acids (PUFA). PUFAs compete during the vulcanization process with multiple components of a functional rubber compound. Esterified propoxylated glycerol oils do not require PUFA to maintain suitable pour points and will not compete with rubber components during the vulcanization process. It has been found that natural oils can provide performance advantages in tire formulations. Specifically, natural oils, such as soybean oil, have been found to lower the glass transition of tires creating better cold weather performance. The use of esterified propoxylated glycerol oils enable tailoring of the performance by lowering the glass transition while optimizing the degree of unsaturation such that an optimal degree of reaction into the formulation can occur. This may include high levels of unsaturation or even completely saturated fatty acids.

Dielectric fluids are used to cool, insulate and protect the internals of electronic devices. Typically, these fluids are used in transformers, capacitors, switches, etc. When used in a transformer, for example, dielectric fluids transport heat from the windings and core of the transformer or connected circuits to cooling surfaces. Where natural oils are susceptible to oxidation and tend to crystallize at ambient outdoor temperatures, esterified propoxylated glycerol base oils are not susceptible to the same degree of oxidation and possess pour points well below those of natural oils.

The lubricant base oil should be miscible with other base fluids for example the mineral oils commercially available as Group I, II, III, and III+ base oils, polyaplhaolefins commercially available as Group IV base oils, and naphthenic, polyalkylene glycol, and esters base oils commercially available as Group V base oils. The lubricating base oil of the present invention may be blended as an additive or compositional modifier to enhance the performance of the formulated base oil. The synthetic lubricant compositions of the present disclosure show high performance and high temperature stability and have lubricating and viscometric properties that exceed those of a mineral lubricating oil. The compositions may comprise other conventional oil additives, e.g. antisludge agents, extreme pressure agents, viscosity modifiers, and antioxidants known in the art.

The composition of the present disclosure is illustrated by the following examples.

EXAMPLES

Examples 1-72

Mapping Compositional Space of Esterified Propoxylated Glycerol(s)

Figure 2:
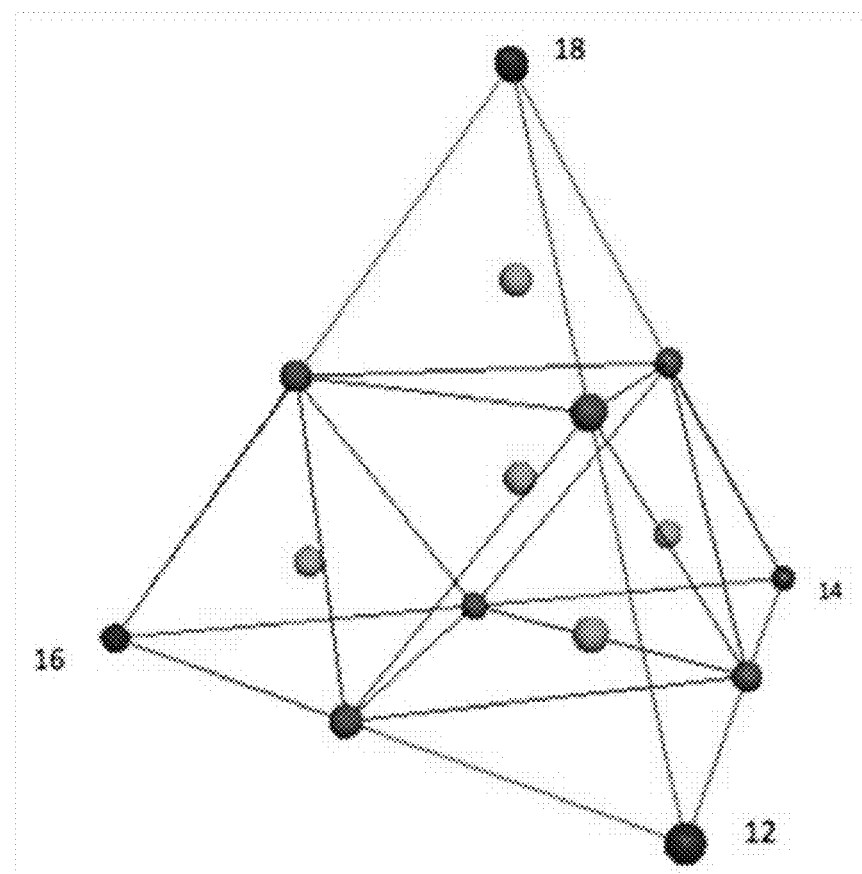
FIG. 2 shows a wireframe rendering of the 3D design space utilized in the demonstration of Examples 1-72.

Given four pure fatty acids (lauric, myristic, palmitic, stearic) we demonstrate the property effects of compositional changes as a function of degree of propoxylation. With 24 example compositions per level of propoxylation (3, 5, 10) we can map property effects across all compositions within the three-dimensional design space for each level of propoxylation as shown in FIG. 2, which shows 3D design space with single fatty acid triesters at the vertices. The results of the mixture design and analysis can be seen in Tables A-C, see FIGS. 3-5. Examples 34, 45, 53, 58, 69 have pour points above 30° C. and were not analyzed for kinematic viscosity.

Figure 6:
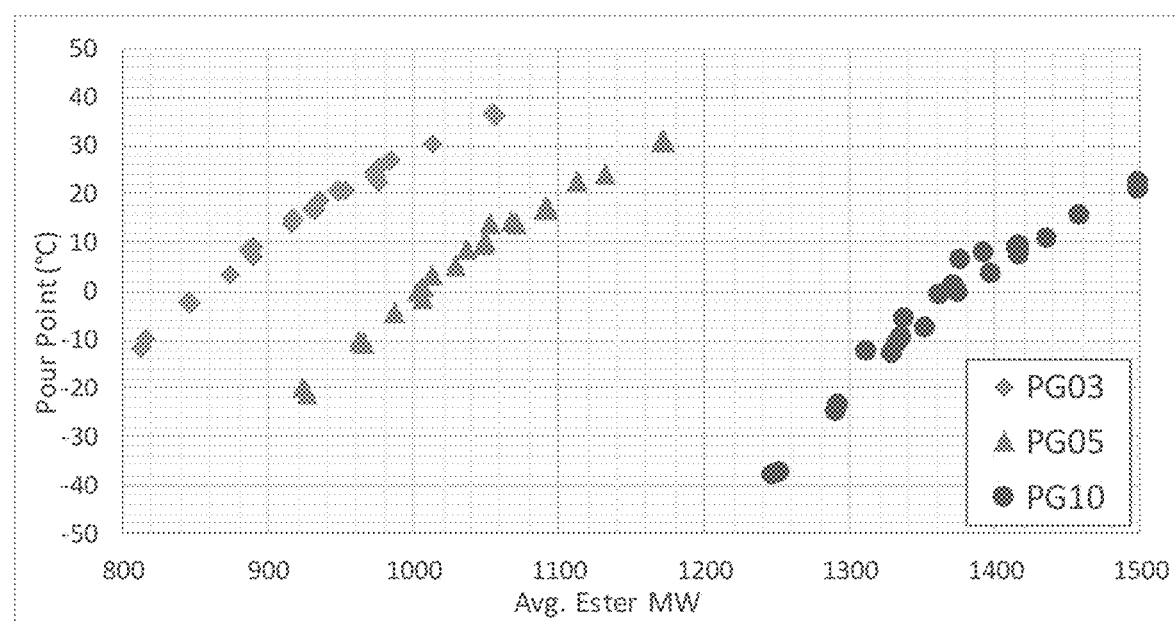
FIG. 6 shows pour point data for examples 1-72 as a function of molecular weight.
Figure 7:
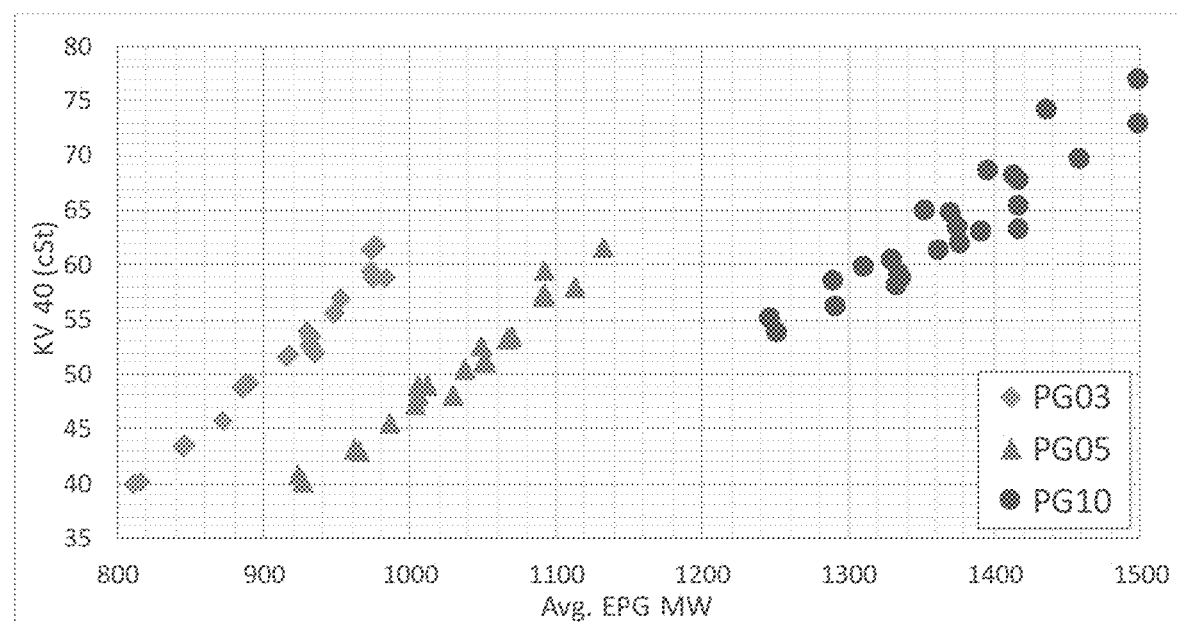
FIG. 7 shows kinematic viscosity (40° C.) data for examples 1-72 as a function of molecular weight.
Figure 8:
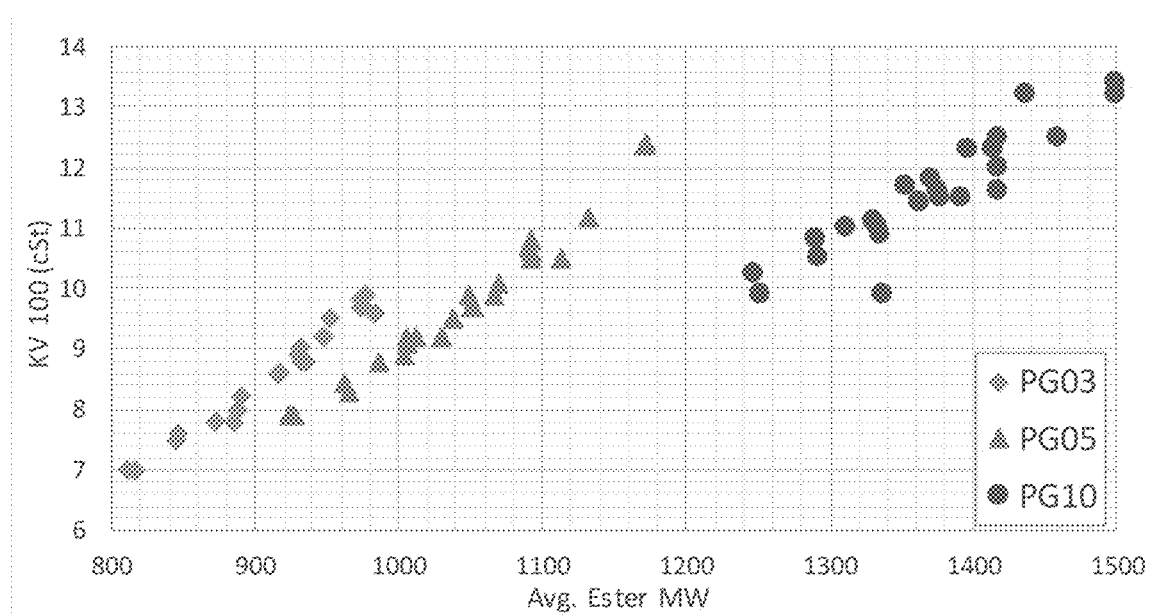
FIG. 8 shows kinematic viscosity (100° C.) data for examples 1-72 as a function of molecular weight.

Average molecular weight was calculated from the fatty acid content and the molecular weight of the propoxylated glycerol. The pour point, see FIG. 6, pour point data vs. average molecular weight for Examples 1-72, and kinematic viscosity data, see FIG. 7 Kinematic viscosity (40° C.) data vs. average molecular weight for Examples 1-72 and FIG. 8 Kinematic viscosity (100° C.) data vs. average molecular weight for Examples 1-72, were plotted against average molecular weight to observe relative effects of changing fatty acid composition and degree of propoxylation. By increasing degree of propoxylation molecular weight increases leading to increased viscosity while simultaneously depressing pour point for comparable fatty acid compositions. FIG. 3 shows Table A, which describes examples 1-24; FIG. 4 shows Table B, which describes Examples 25-48; and FIG. 5 shows Table C, which describes Examples 49-72.

Mapping of the compositional space enables predictive modelling of compositions based on desired performance outputs of the given esterified propoxylated glycerol materials.

Examples 73-79

Base Oil Comparison Versus Commercial Formulated Lubricant

Examples 73-79, see FIG. 9 Table D, consist of esterified propoxylated glycerol base oils prepared as known to those of skill in the art and consisting of fatty acids that are purified sources or whole cut sources. The example base oils (neat and non-additized) were compared against John Deere's HyGard Transmission and Hydraulic Oil which is the standard fluid for meeting the J20c specification for agricultural equipment (Table D).

Esterified propoxylated glycerol lubricating base oils display viscosities characteristic of oils in a given ISO VG range and viscosity indices exceeding commercial mineral oil lubricants. Pour point(s) of the example base oils are also characteristic of fully formulated commercial lubricants.

Examples 80-84

Functional Fatty Acid Modified Esterified Propoxylated Glycerol

Figure 11:
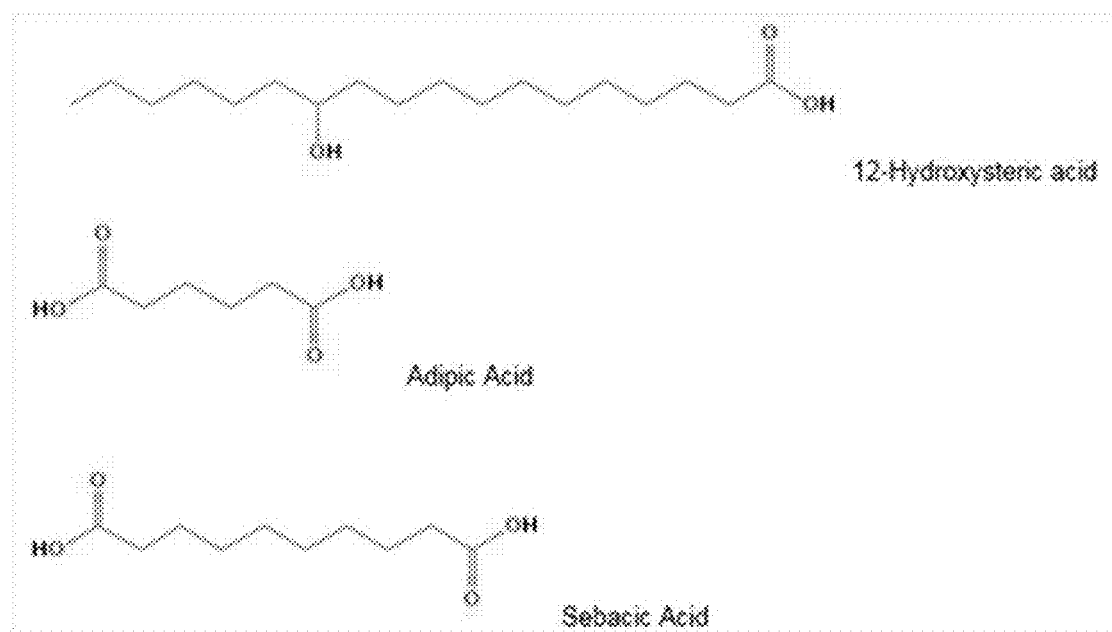
FIG. 11 shows molecular diagrams for adipic, sebacic, and 12-hydroxystearic acids.

Examples 80-84 consist of esterified propoxylated glycerol base oils in which the fatty acid composition has been modified by the addition of diacid components and hydroxy fatty acid components, see FIG. 10 Table E and FIG. 11, Representative functional fatty acids: azelaic, sebacic, and 12-hydroxystearic acids). Example 80 is a base consisting of hydrogenated coconut fatty acids. Examples 81 and 82 consist of hydrogenated coconut fatty acids modified with sebacic (C10) diacid. Examples 83 and 84 consist of hydrogenated coconut fatty acids modified with 12-hydroxystearic acid. Pour point and viscosity of the resultant base oils of the disclosure are clearly impacted by the inclusion of functional fatty acids in the base oil composition.

Example 85

Dielectric Measurements

Example 85, see FIG. 12, consists of esterified propoxylated glycerol base oil, comprising propoxylated glycerol (10 PO) and oleic acid, that was tested for properties characteristic of dielectric fluids, particularly those utilized as transformer fluids. The base oils of the disclosure were compared to commercially available biodegradable transformer fluids, see FIG. 12, Table F.

Examples 86-88

Ethoxylated Glycerol Samples

Examples 86-88 consist of esterified ethoxylated glycerol composed of ethoxylated glycerol Lumulse® 12 (12 ethoxylate units per glycerol) with coconut fatty acids (Example 86), stearic acid (Example 87), and lauric acid (Example 88). Initial pour point analysis and kinematic viscosity analysis is shown in see FIG. 13, Table G.

There has been a growing need and desire for environmentally friendly lubricants whether out of a sense of environmental stewardship or due to mandate based on applications and application areas, but current environmentally friendly options are either too costly or have marked performance issues. Esterified propoxylated glycerol lubricating base oils provides a high-performance environmentally friendly lubricant that is cost comparable to Group III+ mineral oils with performance that exceeds the most costly synthetic lubricants.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed:

1. A synthetic ester comprising:
   at least one propoxylated or butoxylated polyol, wherein an average degree of propoxylation or butoxylation is ≥3;
   at least one fatty acid, wherein the at least one fatty acid is equal to or greater than C4; and
   wherein a hydroxyl value of the synthetic ester is less than 8 mg KOH/g.

2. The synthetic ester of claim 1, wherein the at least one propoxylated or butoxylated polyol comprises glycerol, trimethylol propane, neopentyl glycol, and/or sorbitol.

3. The synthetic ester of claim 1, wherein the at least one propoxylated or butoxylated polyol comprises propoxylated glycerol.

4. The synthetic ester of claim 1, wherein the at least one fatty acid is substantially fully saturated.

5. The synthetic ester of claim 1, wherein the at least one fatty acid is substantially unsaturated.

6. The synthetic ester of claim 1, further comprising at least one additional fatty acid having a chain length of greater than or equal to C4.

7. The synthetic ester of claim 1, wherein a source for the at least one fatty acid comprises >80% whole cut fatty acid.

8. The synthetic ester of claim 1, wherein the at least one fatty acid is a dicarboxylic acid or dimer acid.

9. The synthetic ester of claim 4, wherein the at least one substantially fully saturated fatty acid comprises 12-hydroxystearic acid.

10. The synthetic ester of claim 1, wherein the at least one fatty acid is functionalized.

11. The synthetic ester of claim 10, wherein the functionalization comprises epoxidation, maleination, metathesis, amidation, halogenation, hydration, estolide formation, and/or vulcanization.

12. The synthetic ester of claim 1, wherein the synthetic ester has a pour point of at or below −10° C.

13. The synthetic ester of claim 1, wherein the synthetic ester is at least 60 percent biodegradable.

14. The synthetic ester of claim 1, wherein the synthetic ester is at least 50 percent bio-based.

15. The synthetic ester of claim 1, wherein the synthetic ester forms a base oil.

16. The synthetic ester of claim 1, wherein the synthetic ester comprises a process oil or rubber extender oil.

17. The synthetic ester of claim 1, wherein the synthetic ester comprises a dielectric fluid.

18. A method for forming a synthetic ester comprising:
   propoxylating or butoxylating at least one polyol backbone, wherein an average degree of propoxylation or butoxylation is from ≥3;
   esterifying the at least one propoxylated or butoxylated polyol backbone with at least one fatty acid, wherein the at least one fatty acid is equal to or greater than C4; and
   wherein the hydroxyl value of the synthetic ester is less than 8 mg KOH/g.

19. The synthetic ester of claim 1 comprising a mixture of at least one aqueous solution, at least one aliphatic hydrocarbon fluid, at least one aromatic hydrocarbon fluid, at least one triglycerides fluid, at least one synthetic ester fluid, at least one polyolefin fluid, and/or at least one glycol fluid, wherein the synthetic ester comprises from 0-10% or 90-100% of the mixture.

* * * * *

UNITED STATES PATENT AND TRADEMARK OFFICE
CERTIFICATE OF CORRECTION

PATENT NO. : 11,807,826 B2
APPLICATION NO. : 17/552418
DATED : November 7, 2023
INVENTOR(S) : Zachary Hunt et al.

It is certified that error appears in the above-identified patent and that said Letters Patent is hereby corrected as shown below:

On the Title Page

Item (73), "University of South Carolina, Columbia, SC (US)" should read --Tetramer Technologies, LLC, Pendleton, SC (US)--

Signed and Sealed this
Fourth Day of June, 2024

Katherine Kelly Vidal
*Director of the United States Patent and Trademark Office*